United States Patent [19]

Yeoman et al.

[11] 4,234,519

[45] Nov. 18, 1980

[54] RECOVERY OF METHACROLEIN

[75] Inventors: Neil Yeoman, Merick; Sidney S. Stern, New York, both of N.Y.

[73] Assignee: Halcon Research and Development Corp., New York, N.Y.

[21] Appl. No.: 6,824

[22] Filed: Jan. 26, 1979

[51] Int. Cl.³ .................. C07C 45/35; C07C 47/21
[52] U.S. Cl. .................................................. 568/492
[58] Field of Search .................. 260/604 R; 560/532, 560/533

[56] References Cited

U.S. PATENT DOCUMENTS

| | | | |
|---|---|---|---|
| 3,097,215 | 7/1963 | Courter et al. | 260/604 R |
| 3,162,514 | 12/1964 | Roelen et al. | 260/604 R |
| 3,405,172 | 10/1968 | Brown et al. | 562/532 |
| 3,433,840 | 3/1969 | Shima et al. | 260/604 R |
| 3,717,675 | 2/1973 | Sennewald et al. | 562/532 |
| 3,972,920 | 8/1976 | Ishii et al. | 260/604 R |
| 4,124,634 | 11/1978 | Gotoh et al. | 260/604 R |
| 4,127,603 | 11/1978 | Bljumberg et al. | 260/604 R |
| 4,147,885 | 4/1979 | Shimizu et al. | 260/604 R |

*Primary Examiner*—Werren B. Lone
*Attorney, Agent, or Firm*—William C. Long; David Dick; Harold N. Wells

[57] ABSTRACT

In the catalytic oxidation of isobutylene and/or tertiary butyl alcohol to methacrolein, the product methacrolein is recovered as an aqueous solution, which thereafter is stripped of methacrolein by contacting the solution with recycle gases from the subsequent oxidation of methacrolein to methacrylic acid. In a preferred embodiment, the oxidation reactor effluent gases are quenched to near ambient temperatures by direct contact with a recirculating stream of partially condensed effluent to provide an aqueous solution of methacrolein and thereafter the methacrolein remaining in the effluent gases is absorbed into a refrigerated water stream to provide a second aqueous solution. The aqueous solutions are combined and stripped by recycle gases, thereby supplying methacrolein as feed to the subsequent oxidation process.

5 Claims, 1 Drawing Figure

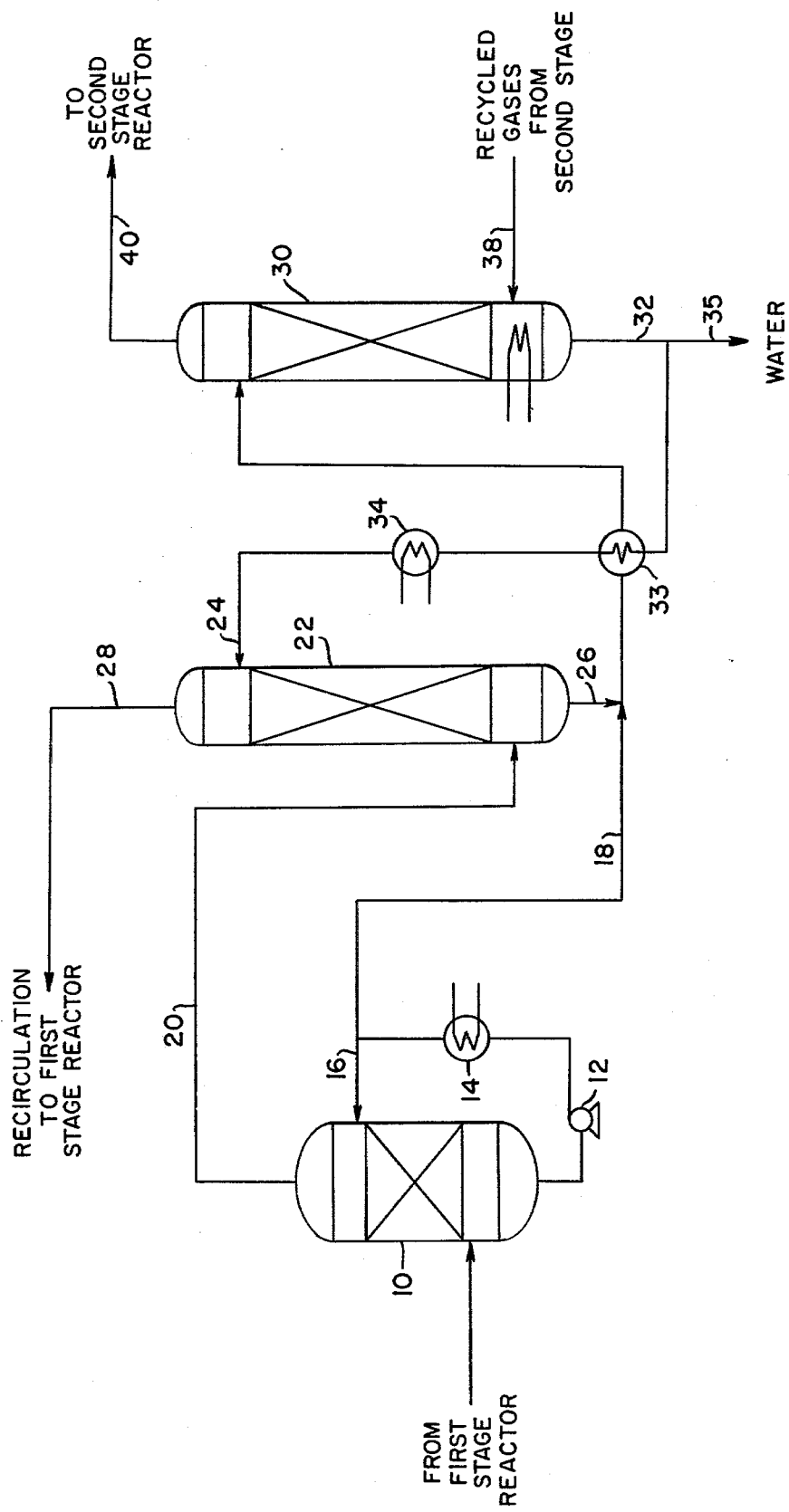

RECOVERY OF METHACROLEIN

PRIOR ART

This invention relates generally to the recovery of methacrolein from the gaseous effluent from the catalyst oxidation of isobutylene or tertiary butyl alcohol. More specifically, the invention relates to an improved process for purification of methacrolein and for introduction of the purified methacrolein into a downstream oxidation step wherein the methacrolein is oxidized to methacrylic acid.

The preparation of methacrolein by the catalytic oxidation of isobutylene and/or tertiary butyl alcohol (which is dehydrated to isobutylene in the reaction zone) is a known reaction described, for example, in Ishii, et al., U.S. Pat. No. 3,972,920, or in Khoobiar, U.S. Pat. No. 4,087,382. In processes of this type, isobutylene and/or tertiary butyl alcohol are typically mixed with oxygen, e.g. as air, an inert gas such as nitrogen, carbon dioxide, and the like, and steam, and the resulting mixture is oxidized at temperatures generally ranging between 300° C. and 500° C. in the presence of a suitable catalyst, such as the one described in the above-mentioned patent, the gaseous reaction product comprising, in addition to methacrolein, unreacted isobutylene, unreacted oxygen, large amounts of inert gases and steam and minor amounts of organic by-products such as aldehydes, aliphatic acids, ketones, and the like.

Since the amount of methacrolein typically is a relatively small proportion of the effluent stream, say less than 5 volume %, recovery of the methacrolein presents a difficult task, particularly since it is associated with a number of impurities which must be removed prior to further processing to produce methacrylic acid. The use of water washing to absorb methacrolein has been suggested in the prior art. As an example, in U.S. Pat. No. 3,162,514, Roelen, et al., pointed out that the amount of water involved for the recovery is very large and results in large investments and high operating costs to carry out the necessary distillation of methacrolein from water solutions. Roelen, et al., further note that the distillation is complicated by the fact that a number of the products of the oxidation of olefins to aldehydes form azeotropic mixtures with water. They disclose an improved method of recovery in which the gases from the oxidation reactor are cooled in two stages to remove as much of the water as possible, followed by removal of the aldehyde portion by ketone scrubbing. The two stages of cooling involve water cooling to near ambient temperatures, followed by refrigeration for additional water condensation, preferably to between −20° and −30° C. The rich solvent from ketone scrubbing is stripped and the aldehyde recovered. Despite the substantial cooling carried out by the process of the '514 patent, the bulk of the aldehydes were recovered by ketone washing of the gas phase rather than as dissolved components in the condensed water. No additional water was added so that the Roelen, et al., process is not considered to be a water scrubbing process. The patentees' process has the disadvantage of requiring the removal of the scrubbing agent from the methacrolein if it is to be further oxidized to methacrylic acid.

Another process in which methacrolein is absorbed by a solvent is disclosed in U.S. Pat. No. 4,092,132 to Leacock, in which acetic acid is used to recover methacrolein. Acetic acid is disclosed to have inherent advantages over processes, such as that of Roelen, in which other solvents are employed however, acetic acid absorbs both methacrolein and unreacted isobutylene which must be separated. Reference is made in the Leacock patent to another patent application (Ser. No. 830,736) in which effluent gases from the catalytic oxidation of isobutylene or tertiary butyl alcohol are quenched under graduated increasing pressure. Water is condensed from the gases as pressure is increased and is separated, leaving the gases relatively dry when they are later contacted with acetic acid to recover methacrolein. The water which is condensed and separated contains only a minor amount of methacrolein and thus the process disclosed by Leacock is not a water scrubbing process.

In U.S. Pat. No. 3,097,215, Courter, et al., disclose a process for recovery of aldehydes by successive steps in which water is added in order to fully recover the aldehyde from the reactor effluent. In the first stage, a portion of the water content is condensed, leaving the bulk of the aldehyde in the vapor phase. After separation, both the liquid and vapor phases are pressured to a substantially higher pressure (125–300 psia is suggested) and fed to a high pressure absorber where water is added to absorb the aldehyde content of the gas. Rich water from the absorber is distilled in order to recover the aldehydes and to strip the water for recycling to the absorption step. A principal feature of the '215 patent is the use of higher pressures in the absorption tower in order to minimize the use of additional water and thereby to gain an advantage over conventional scrubbing processes carried out at low pressures.

In U.S. Pat. No. 3,433,840, Shima, et al., disclose a process for recovery of acrolein from a propylene oxidation reactor effluent by quenching with recirculating condensate, followed by water scrubbing of the gas which is not condensed in the quenching step. The patentees were concerned with the removal of impurities which were found to cause substantial difficulties in the acrolein recovery towers and provided for steam stripping of the water condensed in the quenching step. By removing heavy impurities, the patentees found that a substantial improvement in the operability of the absorption equipment was obtained. The initial quenching step was carried out at relatively high temperatures of 30°–80° C., which was found to be sufficient to remove impurities. Recovery of the acrolein was carried out by water scrubbing at a temperature between 0°–30° C. followed by distillation in order to separate acrolein from the water used for absorption. Such a process is subject to the objections noted by Roelen, et al., namely, that high costs are involved in the separation of water and methacrolein by distillation.

Still further improvements have been sought in the recovery and purification of methacrolein from gaseous streams prior to the catalytic oxidation of methacrolein to methacrylic acid. Such an improvement has been discovered by the inventors and is disclosed and claimed hereinafter.

SUMMARY OF THE INVENTION

The invention relates to a process for recovering and purifying methacrolein produced by the vapor phase catalytic oxidation of isobutylene and/or tertiary butyl alcohol with molecular oxygen. The effluent from the oxidation reaction typically is at a temperature of about 340°–430° C. depending upon the activity of the catalyst and the degree of conversion desired, and a pressure of about 1.4–2.5 kg/cm² gauge. Methacrolein is recovered from the reactor effluent gases by absorption into water and thereafter the methacrolein is stripped from the water with recycle vapors derived from the recovery of methacrylic acid precedent to their being returned to the catalytic oxidation of methacrolein to methacrylic acid. In a preferred embodiment, the effluent gases are first quenched to a temperature near ambient by direct contact with a recirculating stream of partially condensed effluent to provide an aqueous solution of methacrolein and thereafter the methacrolein remaining in the effluent gases is absorbed into a refrigerated water stream to provide a second aqueous solution. Both aqueous solutions are combined and stripped by recycle gases, thereby supplying methacrolein as feed to the subsequent oxidation process.

BRIEF DESCRIPTION OF THE DRAWING

The sole FIGURE is a flow diagram of the preferred process for recovery of methacrolein according to the invention.

DESCRIPTION OF THE PREFERRED EMBODIMENTS

The process for recovery of methacrolein to be described is associated with the two-stage oxidation of isobutylene (and/or tertiary butyl alcohol) to methacrylic acid, such as has been disclosed generally in the prior art. It has generally been found preferable to carry out the oxidation in two stages rather than a single stage in order to obtain maximum efficiency of the conversion of the isobutylene to methacryic acid. Since the feed to the second oxidation stage should contain essentially only methacrolein and unreacted isobutylene should be recycled to the first oxidation stage, the methacrolein produced in the first stage oxidation process is separated and purified. The gases leaving the first stage reactor, typically will be at a temperature in the range of 340°–430° C., a pressure of about 1.4–2.5 kg/cm² gauge, and will contain methacrolein, water, unreacted isobutylene, by-product oxygenated hydrocarbon impurities, such as acetic and acrylic acids, and the inert gases, such as nitrogen, oxygen, and carbon oxides.

The preferred recovery scheme of the invention is illustrated diagrammatically in the FIGURE, beginning with the effluent gases from the first stage oxidation and ending with the disposition of the separated methacrolein into the feed gases entering the second stage oxidation. Neither of the oxidation stages, however, are shown in the FIGURE. Since the gases are exiting the first stage reactor at a relatively high temperature, they may be used to generate steam or otherwise recover heat evolved in the oxidation of isobutylene. Such a heat recovery step would be carried out in conventional facilities which are not shown in the FIGURE. Alternatively, heat could be merely rejected to water or air. In the preferred embodiment of the invention shown in the FIGURE, methacrolein is recovered by absorption in water by a two-stage process. Alternatively, it is within the broadest scope of the invention to employ only a single absorption stage, as by deleting quench tower 10 and its associated facilities, although such an arrangement would be less economic and, accordingly, is not preferred.

The temperature of the gases entering the quench tower 10 may be at any value between the reactor outlet temperature and the temperature of the quench system, depending upon the relative economics of various cooling schemes. Typically, the temperature of the gases entering the quench column 10 may be about 150° C., and no water will have been condensed. As the still warm gases enter the quench tower, they are countercurrently contacted with a recirculating stream derived from condensation of the gases. As the gases rise through the tower 10, they are cooled and water is condensed, along with some of the impurities and only minor amounts of methacrolein. The temperature of the gas leaving the top of the quench tower 10 will be close to that of the inlet quench liquid. Heat released by condensation of vapor raises the temperature of the recirculating liquid to a degree dependent upon the amount of recirculation employed. The recirculation pump 12 passes the condensate to heat exchanger 14, where the heat of condensation is removed by water or other suitable cooling means and returns the cooled liquid to column 10 via line 16. It will be understood by those skilled in the art that more than one quenching stage could be provided if desired. Contacting of the gases and recirculating liquid is carried out in the tower by means of trays, packing, or other devices known to those skilled in the art. A portion of the recirculating stream equivalent to the amount of water, methacrolein, impurities condensed from the gas stream is withdrawn continually and passed to the stripping column 30 via line 18, to be discussed later.

The gas stream passes overhead from the quench tower via line 20 and enters the bottom of the methacrolein absorber 22 where it is contacted countercurrently with a refrigerated water stream which enters at the top of the absorption column via line 24. Conditions in the absorber column are adjusted so that essentially all of the methacrolein produced by the oxidation of isobutylene is absorbed into the liquid leaving the bottom of the column via line 26, which contains about 1 mol % methacrolein. The gases leaving the top of column 22 via line 28 are substantially free of methacrolein, but still contain the inert gases and unreacted isobutylene, which can be recirculated to the first stage oxidation for more complete usage of the isobutylene feed stock if desired. If the source of molecular oxygen used in the first stage oxidation is air, a substantial amount of nitrogen must be purged from the gas (not shown) in an amount equivalent to the nitrogen in the incoming fresh air in order to avoid undue dilution of the reaction gases by the recycling of the gas in line 28. In the event that molecular oxygen is added in the form of pure oxygen or enriched air, the purge of nitrogen may be significantly reduced or eliminated altogether. Water entering the top of column 22 may be fresh water used in a once-through absorption of methacrolein. Preferably, the water will be recirculated from the bottom of the stripping column 30 which is still to be discussed. The temperature of the water entering via line 24 will be adjusted to a desired temperature, preferably below ambient, in order to provide the most efficient recovery of methacrolein. The pressure of the absorption column 22 should be kept as high as possible in order to minimize the amount of water needed. However, the pressure of column 22 is generally determined by the pressure of the first oxidation stage and pressure drop through upstream equipment. Although pressure is not easily varied without introducing gas compression, such a mode of operation is considered to be within the broad scope of the invention. It will be understood that the optimum pressure and temperature of the absorption column, as well as the amount of water used will be determined by economic considerations familiar to those skilled in the art. That is, either cold water (below ambient) and low pressure or warm water and higher pressure may be used to absorb methacrolein. As with the quench tower 10, the absorption column 22 will also use trays, packing or other suitable devices for contacting the effluent gases with refrigerated water.

Liquid from the bottom of the absorption column 22 is passed to the stripping column 30 via line 26. Line 18, carrying condensate from the quench tower 10 joins line 26. Before contacting the stripping gas in column 30, the feed water may be flashed to remove any residual isobutylene, which would be returned to the absorption column 22. The FIGURE illustrates a typical heat recovery step accomplished by exchanger 33 which heats the feed to column 30 by cooling the recirculating water in line 24. Methacrolein is stripped in column 30 from the water by countercurrently contacting with recycled gases from the second oxidation stage which enter via line 38. Thus, in a single step, methacrolein is both recovered and introduced to the second stage reactor via line 40. The amount of the gases used will be determined principally by the amount required to carry out the stripping of methacrolein most efficiently up to the maximum amount of recycle gases available. As with the columns already discussed, the stripping tower 30 will be provided with trays, packing or other suitable devices for contacting the liquid and gas streams. Although as illustrated the stripping gas enters tower 30 below the bottom tray, it will be understood that the gas may be introduced higher in the column, thereby including trays for steam stripping of the water to remove compounds absorbed from the recycle gas. Liquid leaving the bottom of column 30 via line 32 is essentially water containing minor amounts of impurities that may be stripped out or otherwise disposed of if water is used in a once-through basis, but preferably the water will be returned to the absorption column 22. Some excess water is typically purged from the methacrolein recovery system via line 35. The recycled water will be chilled in heat exchanger 34, with the refrigeration provided by conventional facilities, such as ammonia refrigeration and the like.

A major advantage of the methacrolein recovery process of the invention is that at no time is methacrolein concentrated, thereby minimizing polymerization problems associated with vaporization of concentrated methacrolein solutions. Prior art methacrolein recovery processes discussed earlier have as an objective preparation of concentrated methacrolein and are undesirable relative to the process of the present invention.

The following presents a detailed description of one embodiment of the invention.

One thousand (1000) moles per hour of the effluent gases leaving the first stage oxidation reactor (not shown) are cooled to a temperature of about 150° C. by generating steam (not shown). The gases enter the quench tower 10 near the bottom which is operated typically at a pressure of about 1 kg/cm² gauge. The gases rise through the quench tower 10 and are contacted by a recirculating condensate stream which enters the tower 10 at a temperature of about 35°–40° C., as determined by the temperature of ambient coolants and optimum heat exchanger design, and, after condensing a portion of the water from the effluent gases, the liquid leaves the quench tower 10 at a temperature of about 60° C., as determined by the amount of liquid recirculation, which for purposes of this example is about 7170 mol/hr. The recirculating stream 16 and the net liquid produced (18) contain about 0.4 mol % methacrolein, 5–6 mol % by-product impurities, and the remainder water. A portion of the recirculating liquid stream, 200 mol/hr, is passed to the stripping column via line 18. Effluent gases leaving the top of the quench tower 10 contain about 5 mol % methacrolein, about 1.5 mol % isobutylene, about 0.4 mol % impurities, and the remainder essentially only inert gases. The gas enters the absorption column 22 which also is operated at about 1 kg/cm² gauge and passes countercurrently upward against the flow of refrigerated water entering the top of the column via line 24 at a temperature of about 3°–5° C., and, as a result of the condensation which occurs in the absorption column 22, leaves the column via line 26 at a temperature of about 15°–20° C. Essentially all of the methacrolein is absorbed in the water stream so that at the bottom of the column it contains about 1.1 mol % methacrolein, about 4.6 mol % by-product impurities, and the remainder water. Gases leaving the top of the absorption column via line 28 contain only a trace of methacrolein, approximately 1.7 mol % isobutylene and the remainder inert gases. The combined liquid streams from and the remainder inert gases. The combined liquid streams from the quench tower 10 and the absorption column 22 are passed via line 28 to the top of the stripping column 30 which is operated at a pressure of about 1.4 kg/cm² gauge. Recycle gas (680 mol/hr) from the second stage oxidation enters the stripping column 30 via line 38 with a composition of approximately 2.9 mol % methacrolein, 0.5 mol % impurities, 7.4 mol % water, and the remainder inert gases. After stripping essentially all of the methacrolein from the incoming liquid stream, the gas passing overhead of the stripping column via line 40 may be sent directly to the second stage oxidation reactor and contains 7.4 mol % methacrolein, 2.1 mol % impurities and 21.2 mol % water, and the remainder essentially inert gases.

It should be noted that the compositions and flow rates given in the above example may vary depending upon the operating temperatures and pressures chosen. For example, by adjustment of the operating temperature of the stripping column 30, the stripping column's efficiency is optimized, and it is possible to control the amount of water which is sent to the second stage reactor. The stripped water leaving the bottom of the column 30 via line 32 contains only a trace of methacrolein and an equilibrium concentration of various impurities. The stream has a temperature of approximately 120° C., and it will be cooled by heat exchange against other streams and finally by refrigeration to a temperature of about 3°–5° C., although it should be understood that this temperature may be adjusted to optimize the overall efficiency of the water and stripping columns.

The foregoing description of the preferred embodiments of the invention is intended for illustration only and should not be considered as limiting the scope of the invention, which is defined by the claims which follow.

What is claimed is:

1. A process for recovering methacrolein from effluent gases produced by the vapor-phse catalytic oxidation of isobutylene and/or tertiary butyl alcohol with molecular oxygen in the presence of a catalyst at a temperature of 300°–500° C. and supplying said methacrolein to a subsequent catalytic oxidation to methacrylic acid comprising:

(a) cooling and condensing said effluent gases by direct contact with water to provide a gas stream and an aqueous solution of methacrolein;

(b) stripping said aqueous solution of (a) with recycle gas vapors derived from the recovery of said methacrylic acid precedent to the use of said vapors in said subsequent catalytic oxidation of methacrolein to methacrylic acid to desorb substantially all of the methacrolein absorbed in (a), whereby said methacrolein is added to said vapors as feed to said subsequent oxidation.

2. A process for recovering methacrolein from effluent gases produced by the vapor-phase catalytic oxidation of isobutylene and/or tertiary butyl alcohol with molecular oxygen in the presence of a catalyst at a temperature of 300°–500° C. and supplying said methacrolein to a subsequent catalytic oxidation to methacrylic acid comprising:

(a) cooling and condensing said effluent gases by direct contact with a recirculating stream of condensate from said gaseous stream and withdrawing the net amount of said condensate and a gas stream comprising the uncondensed portion of said effluent gases;

(b) scrubbing said gas stream of (a) with a water stream having a temperature below ambient to absorb substantially all of the methacrolein content of said gas stream as a water solution of methacrolein;

(c) stripping said water solution of (b) and the condensate portion of (a) with recycle vapors derived from the recovery of said methacrylic acid precedent to the use of said vapors in said subsequent catalytic oxidation of methacrolein to methacrylic acid to desorb substantially all of the methacrolein absorbed in the water stream of (b) and the condensate portion of (a), whereby said methacrolein is added to said vapors as feed to said subsequent oxidation.

3. The process of claim 2 wherein said water stream of (b) comprises the water solution of (c) after the removal of methacrolein therefrom.

4. A process for recovering methacrolein from a gaseous stream produced by the vapor-phase catalyst oxidation of isobutylene and/or tertiary butyl alcohol with molecular oxygen in the presence of a catalyst at a temperature of 300°–500° C. wherein said gaseous stream is cooled and condensed by direct contact with a recirculating stream of condensate and recovering the net condensed liquid and a gas stream comprising the uncondensed portion of said gaseous stream which is thereafter scrubbed with a water stream at a temperature below ambient to remove substantially all the methacrolein content of said gas stream, the methacrolein being thereafter supplied to a subsequent catalytic oxidation to methacrylic acid the improvement comprising stripping the water stream containing methacrolein with recycle vapors derived from the recovery of said methacrylic acid precedent to use of said vapors in said subsequent catalytic oxidation of methacrolein to methacrylic acid to desorb substantially all of the methacrolein absorbed in the scrubbing of said gaseous stream and in said net condensed liquid and thereby adding said methacrolein to said recycle vapors as feed to said subsequent oxidation.

5. The process of claim 4 wherein after said water stream containing methacrolein is stripped of methacrolein said water stream is recycled for use in scrubbing methacrolein from said gas stream.

* * * * *